(12) United States Patent
Wagner et al.

(10) Patent No.: US 8,273,793 B2
(45) Date of Patent: Sep. 25, 2012

(54) METHOD FOR PRODUCING PRECURSORS FOR L-2- [$^{18}$F] FLUOROPHENYLALANINE AND 6- [$^{18}$F] FLUORO-L—META-TYROSINE AND THE α-METHYLATED DERIVATIVES THEREOF, PRECURSOR, AND METHOD FOR PRODUCING L-2- [$^{18}$F] FLUOROPHENYLALANINE AND 6- [$^{18}$F] FLUORO-L-META-TYROSINE AND THE α-METHYLATED DERIVATIVES FROM THE PRECURSOR

(75) Inventors: Franziska Wagner, Hergolding (DE); Johannes Ermert, Koeln (DE); Heinrich Hubert Coenen, Grevenbroich (DE)

(73) Assignee: Forschungszentrum Juelich GmbH, Juelich (DE)

( * ) Notice: Subject to any disclaimer, the term of this patent is extended or adjusted under 35 U.S.C. 154(b) by 207 days.

(21) Appl. No.: 12/734,922

(22) PCT Filed: Nov. 21, 2008

(86) PCT No.: PCT/DE2008/001936
§ 371 (c)(1), (2), (4) Date: Jun. 25, 2010

(87) PCT Pub. No.: WO2009/071050
PCT Pub. Date: Jun. 11, 2009

(65) Prior Publication Data
US 2010/0256389 A1    Oct. 7, 2010

(30) Foreign Application Priority Data
Dec. 7, 2007 (DE) .................. 10 2007 059 314

(51) Int. Cl.
A61K 31/4152 (2006.01)
A61K 31/198 (2006.01)
C07D 233/38 (2006.01)
C07C 229/36 (2006.01)

(52) U.S. Cl. ............ 514/567; 514/386; 548/322.5; 562/443

(58) Field of Classification Search ............... 514/567, 514/386; 548/322.5; 562/443
See application file for complete search history.

(56) References Cited

U.S. PATENT DOCUMENTS
2006/0241318 A1    10/2006    Machulla et al.

FOREIGN PATENT DOCUMENTS
WO    WO-2005/037737    4/2005

OTHER PUBLICATIONS
Kuroda et al. Bull. Chem. Soc. Jpn. 2000, 73, 417-422.*

(Continued)

*Primary Examiner* — Joseph Kosack
*Assistant Examiner* — Matthew Coughlin
(74) *Attorney, Agent, or Firm* — Jordan and Hamburg LLP

(57) ABSTRACT

Disclosed is a method for producing precursors for 2-[$^{18}$F] fluorophenylalanine and 6-[$^{18}$F]fluoro-L-meta-tyrosine and the α-methylated derivatives thereof, to the precursor, and to a method for producing 2-[$^{18}$F]fluorophenylalanine and 6-[$^{18}$F]fluoro-L-meta-tyrosine and the α-methylated derivatives thereof from particular precursor. A compound of formula (3) is provided which enables an automated synthesis of L-3,4-dihydroxy-6-[$^{18}$F]fluorophenylalanine and 6-[$^{18}$F] fluoro-L-meta-tyrosine. The enantiomeric purity of the product is ≧98%.

16 Claims, 5 Drawing Sheets

OTHER PUBLICATIONS

Namavari et al. Appl. Radiat. Isot. 1993, 44, 527-536.*
Kuroda et al. Bull. Chem. So. Jpn. 2000, 73, 417-422.*
Tierling T et al: "A new nucleophilic asymmetric synthesis of 6-[18F] Fluoro-DOPA" Journal of Labelled Compounds and Radiopharmaceuticals, John Wiley, Chichester, GB, Bd. 44, Nr. suppl. 1, Jan. 1, 2001, pp. 145-146, XP009113825 ISSN: 0362-4803, cited in the application the whole document.
Namavari M et al: "Synthesis of 6-[<18>F] and 4-[<18>F]fluoro-1-m-tyrosines via regioselective radiofluorodestannylation" Applied Radiation and Isotopes, Elsevier, Oxford, GB, vol. 44, No. 3, Mar. 1, 1993, pp. 527-536, XP024685368 ISSN: 0969-8043 [retrieved on Mar. 1, 1993] the whole document.
Pages T et al.: "Fluorination of aromatic compounds from 1-aryl-3, 3-dimethyltriazenes and fluoride anions in acidic medium—2. Synthesis of (S)-[<18>F]-3-fluoro-alpha-methylphenylala nine" Journal of Fluorine Chemistry, Elsevier, NL, vol. 107, No. 2, Feb. 1, 2001, pp. 329-335, XP004315016 ISSN: 0022-1139, p. 330-334; figures Scheme., 1-4; table 1.
Shen et al: "Decarbonylation of multi-substituted [<18>F]benzaldehydes for modelling syntheses of <18>F-labelled aromatic amino acids" Applied Radiation and Isotopes, Elsevier, Oxford, GB, vol. 65, No. 11, Oct. 17, 2007, pp. 1227-1231, XP022302102 ISSN: 0969-8043 the whole document.
Plenevaux A et al: "Synthesis of non-activated <18>F-fluorinated aromatic compounds through nucleophilic substitution and decarboxylation reactions" Applied Radiation and Isotopes, International Journal of Radiation Applications and Instrumentation, Part A, Pergamon Press LTD, GB, vol. 43, No. 8, Aug. 1, 1992, pp. 1035-1040, XP024706845 ISSN: 0883-2889 [retrieved on Aug. 1, 1992] the whole document.
Synthesis of a Chiral Precursor for No-Carrier-Added (NCA) PET Tracer 6-[18F]Fluoro-L-dopa Based on Regio- and Enantioselective Alkylation of 2,4-Bis(chloromethyl)-5-iodoanisole Chiaki Kuroda, *Atsushi Ochi, Noritoshi Nakane, Takashi Umeyama, Nobuko Muto, Nami Niimura, Yoshiki Teramoto, Hiroyuki Nogami, and Guvvala N. Reddy* Department of Chemistry, Rikkyo University, Nishi-Ikebukuro, Toshima-ku, Tokyo 171-8501 Department of Medical Physics, University of Wisconsin, Madison, WI 53706-1532, USA (Received Jul. 12, 1999).

* cited by examiner

↓ $^{18}F$ fluoridation

↓ Separation and decarbonylation

↓ Hydrolysis and separation

METHOD FOR PRODUCING PRECURSORS FOR L-2-[$^{18}$F] FLUOROPHENYLALANINE AND 6-[$^{18}$F] FLUORO-L—META-TYROSINE AND THE α-METHYLATED DERIVATIVES THEREOF, PRECURSOR, AND METHOD FOR PRODUCING L-2-[$^{18}$F] FLUOROPHENYLALANINE AND 6-[$^{18}$F] FLUORO-L-META-TYROSINE AND THE α-METHYLATED DERIVATIVES FROM THE PRECURSOR

BACKGROUND OF THE INVENTION

The invention relates to a method for producing precursors for 2-[$^{18}$F]fluorophenylalanine (2-[$^{18}$F]FPhe) and 6-[$^{18}$F]fluoro-L-meta-tyrosine (6-[$^{18}$F]FMT) and the α-methylated derivatives thereof, to the precursor, and to a method for producing 2-[$^{18}$F]fluorophenylalanine and 6-[$^{18}$F]fluoro-L-meta-tyrosine and the α-methylated derivatives thereof from the particular precursor.

A publication from the year 2001 by T. Tierling, K. Hamacher, and H. H. Coenen entitled "A new nucleophilic asymmetric synthesis of 6-[$^{18}$F]Fluoro-DOPA", is known, which was published in J. Label. Compds. Radiopharm. 44, Suppl. 1 and which describes a method for producing an [$^{18}$F]FDOPA precursor and the conversion thereof into 6-[$^{18}$F]fluoro-DOPA. According to this method, a precursor is converted into [$^{18}$F]FDOPA using a $K_2CO_3$ cryptand complex by nucleophilic substitution. The product obtained has an enantiomeric purity of 85%.

An electrophilic synthesis of 6-[$^{18}$]- and 4-[$^{18}$F]fluoro-L-meta-tyrosine is known from the article "Synthesis of 6-[$^{18}$]- and 4-[$^{18}$F]Fluoro-L-meta-tyrosines via Regioselective Radiofluorodestannylaton" by the authors M. Namavari et. al. in Appl. Radiat. Isot. Vol 44, No. 3, pp 527-536 from 1993.

The methods for producing 2-[$^{18}$F]FPhe and 2-[$^{18}$F]FMT precursors known from the prior art result in relatively low radiochemical yields and are therefore associated with high cost.

SUMMARY OF THE INVENTION

It is therefore the object of the invention to provide a method for producing 2-[$^{18}$F]FPhe, 6-[$^{18}$F]FMT and the α-methylated derivatives thereof, the precursors thereof, and a method for producing the precursors thereof, which results in greater radiochemical yields and higher enantiomeric purity. In addition, the method should be suited for automated synthesis.

The method and the precursors according to the invention make it possible to produce 2-[$^{18}$F]FPHE, 6-[$^{18}$F]FMT, and the α-methylated derivatives thereof in an enantiopure manner in only three radioactive steps. The synthesis can be carried out in an automated manner and produces enantiomeric purities of ≧98%.

The figures show chemical equations for producing the precursors according to the invention and for producing the target compounds 2-[$^{18}$F]FPhe and 6-[$^{18}$F]FMT and the α-methylated derivatives thereof.

DESCRIPTION OF THE PREFERRED EMBODIMENTS

Formula 1 shows the structure of 2-[$^{18}$F]FPhe and the α-methylated derivative. In the formula, X=H or $CH_3$.

Formula (1)

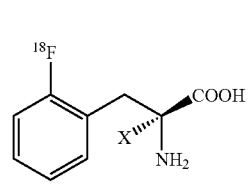

Formula 2 shows the structure of 6-[$^{18}$F]FMT and the α-methylated derivative. In the formula, X=H or $CH_3$.

Formula (2)

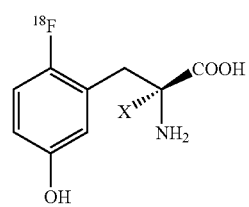

Formula (3) shows the structure of the precursor. In the formula, X=H or $CH_3$.

Formula (3)

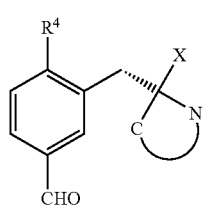

The invention will be explained hereinafter in general terms.

In the formulas and in the figures, the following groups may be provided as the substituents R", X:

$R^1$=Br, I $R^2$=tetrahydropyranyl (THP), methylthiomethyl (MTM), methoxymethyl (MOM), TBDMS, TBDPS, general silyl protecting groups $R^3$=(S)-BOC-BMI: (S)-1-(tert-butoxycarbonyl)-2-tert-butyl-3-methyl-4-imidazolidinone, (S)-Cbz-BMI: (S)-1-(benzoylcarbonyl)-2-tert-butyl-3-methyl-4-imidazolidinone, (S)-BDI: (S)-tert-butyl 2-tert-butyl-4-methoxy-2,5-dihydroimidazol-1-carboxylate, methyl-(S)-BOC-BMI: (2S,5R)-tert-butyl-2-tert-butyl-3,5-dimethyl-4-oxoimidazolidine-1-carboxylate, methyl-(S)-Cbz-BMI: (S)-1-(benzoylcarbonyl)-2-tert-butyl-3,5-dimethyl-4-imidazolidinone or methyl-(S)-BDI: (S)-tert-butyl-2-tert-butyl-5-methyl-4-methoxy-2-hydroimidazol-1-carboxylate Formula notation:

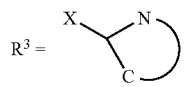

Figure 1:
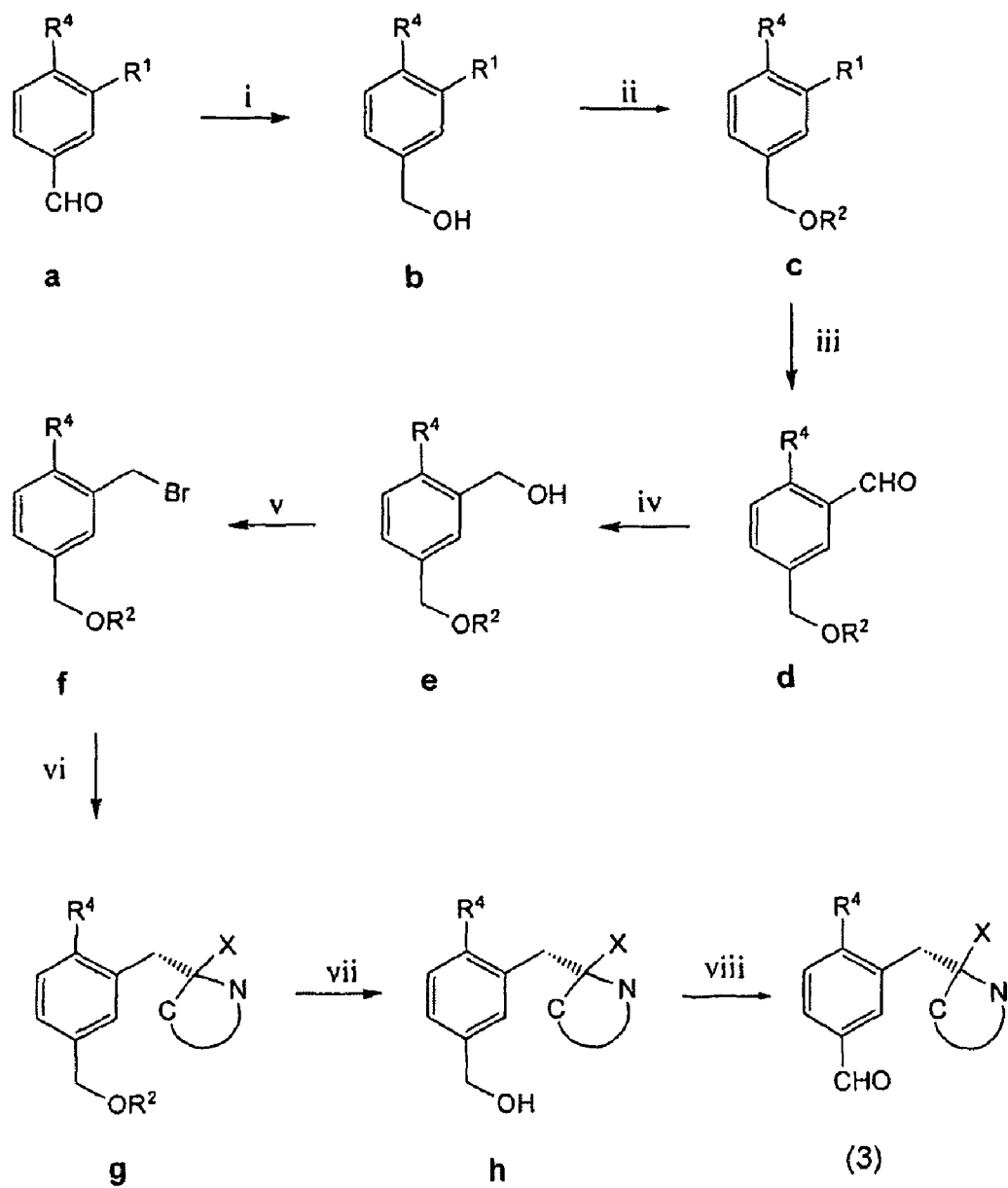
FIG. 1 Shows a general chemical equation for producing the precursor.
Figure 2:
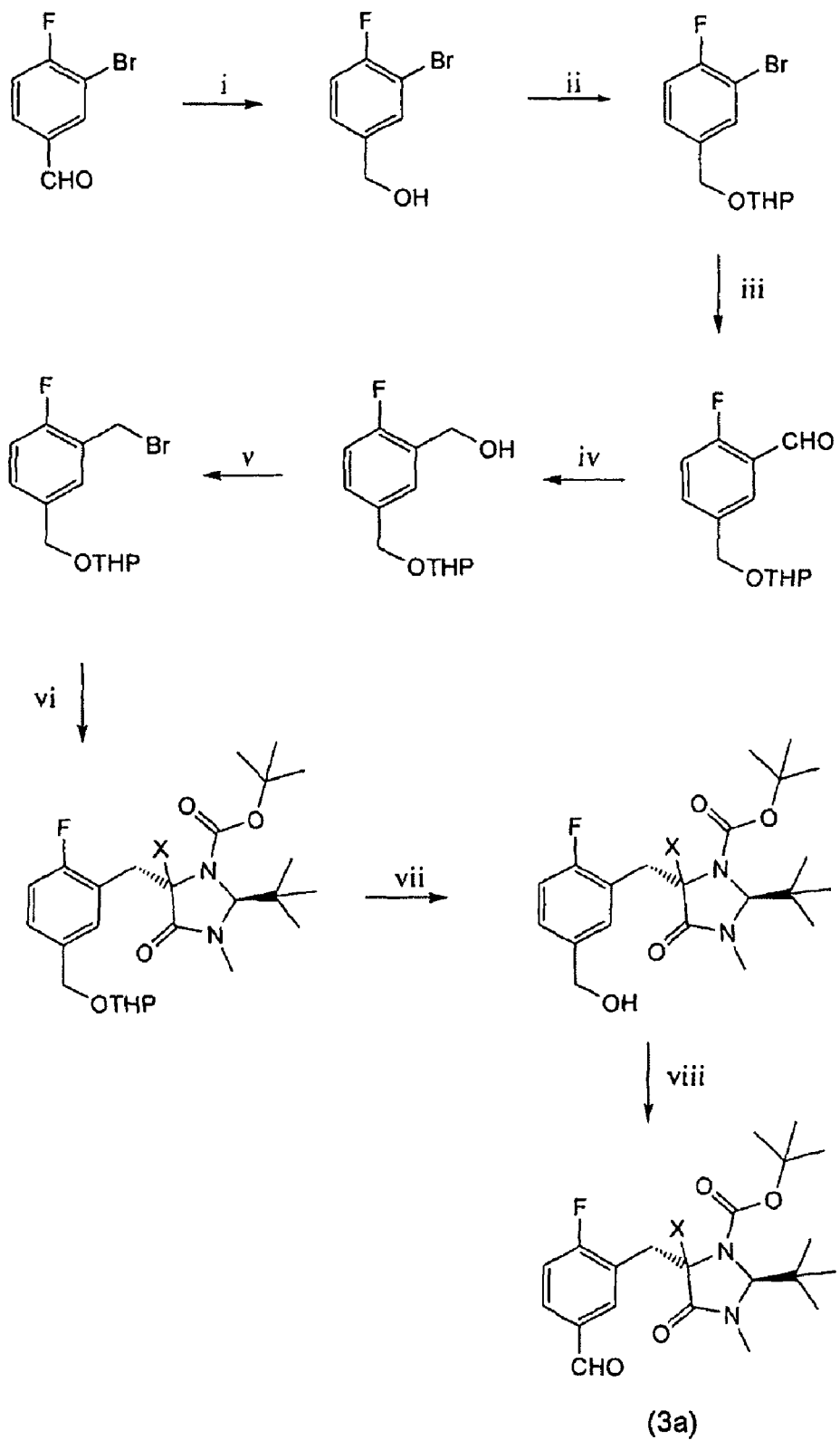
FIG. 2 Shows a chemical equation for the synthesis of the precursor, comprising individual reaction steps.
Figure 2A:
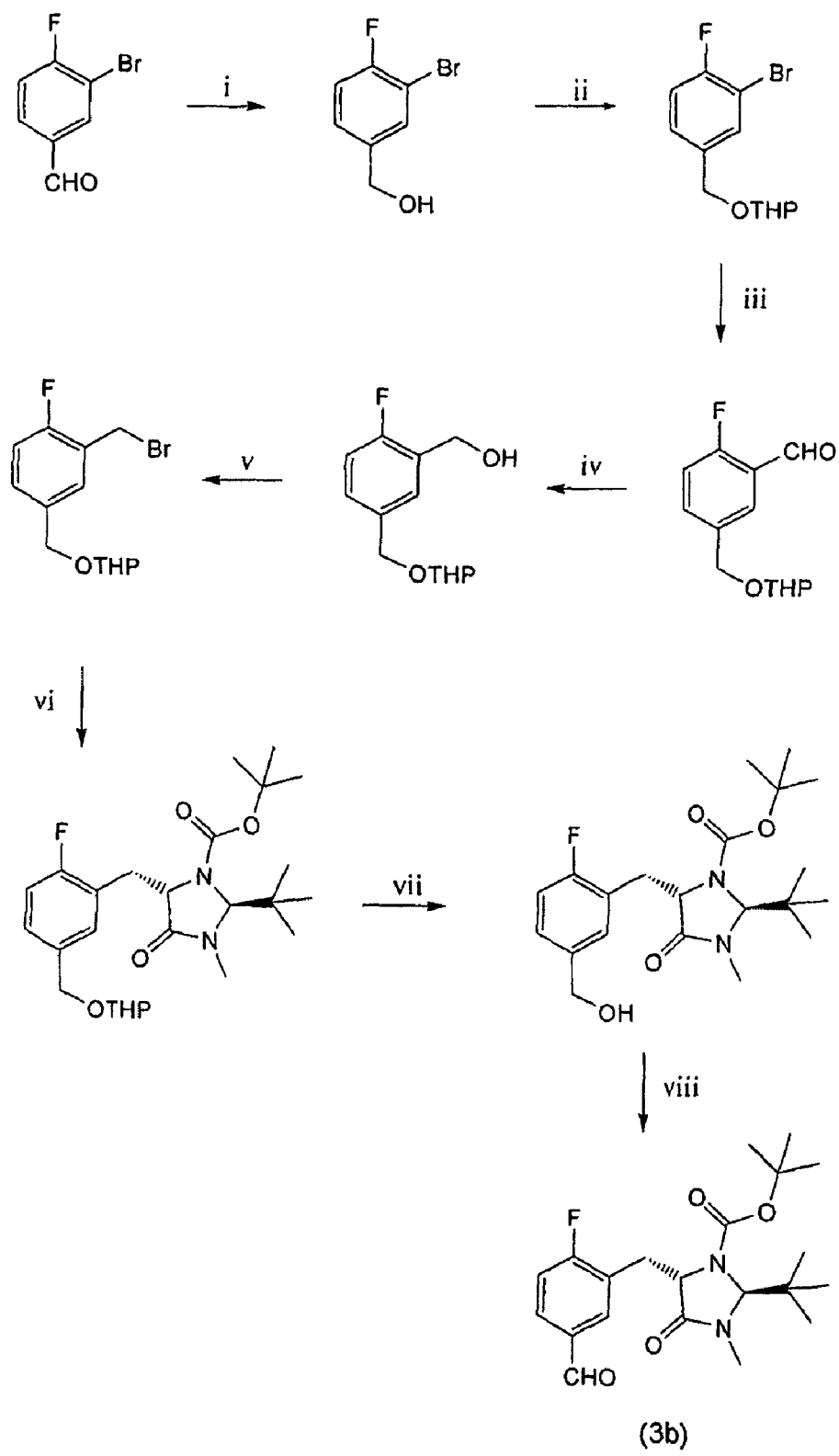
FIG. 2a Shows a special chemical equation for the synthesis of the precursor, comprising individual reaction steps.
Figure 3:
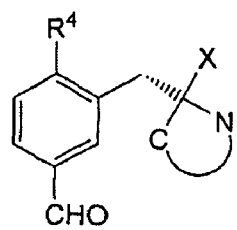
FIG. 3 Shows general steps for producing 2-[$^{18}$F]FPhe and the α-methylated derivative.
Figure 3:
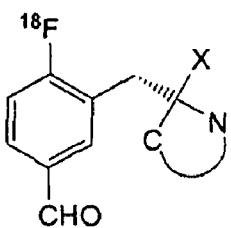
Figure 3:
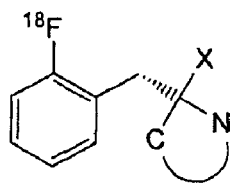
Figure 3:
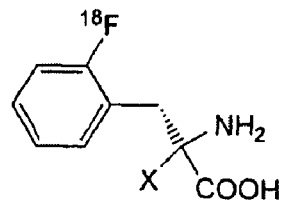
Figure 4:
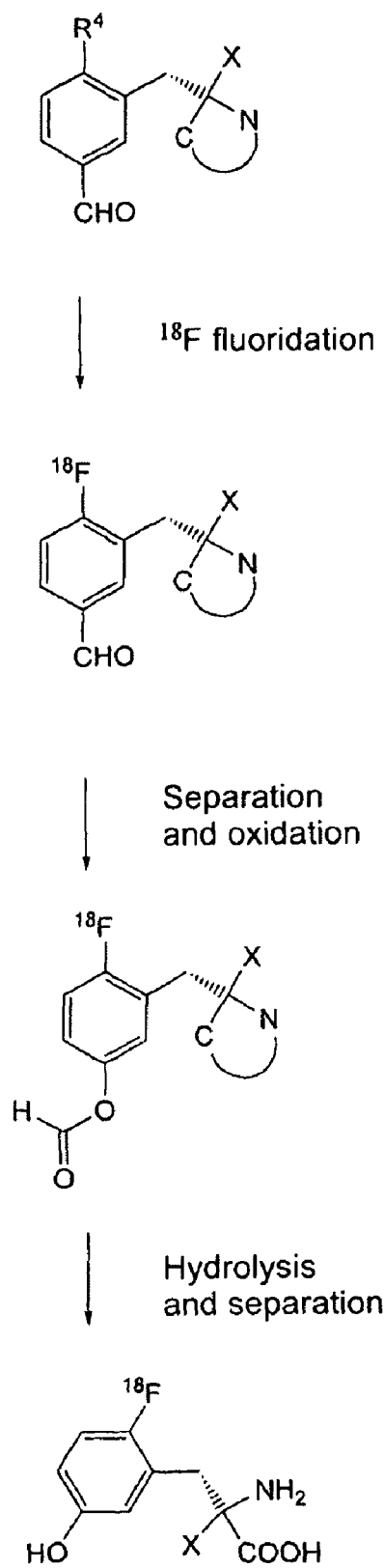
FIG. 4 Shows general steps for producing 6-[$^{18}$F]FMT and the α-methylated derivative.

$R^4$=nucleophilic leaving group, such as F, Br, Cl, $NO_2$, or —$NR_3^+$, where R=alkyl, such as $CH_3$, $C_2H_5$, for example $CH_3$ X=H or $CH_3$ FIG. 1 illustrates a general chemical equation according to which the precursor for 2-[$^{18}$F]FPhe and 6-[$^{18}$F]FMT according to formula 3 can be produced.

The aldehyde group of compound a is reduced in step I.

The reducing agent used can be a metal hydride, such as sodium borohydride or lithium aluminum hydride, for example.

Suitable solvents are methanol or other alcohols, such as ethanol, propanol or isopropanol, in particular when using sodium borohydride.

The reaction is preferably carried out at room temperature.

The production method can be used, by way of example, to produce the compound b as a starting material for the production method for the precursor according to the invention. However, it is also possible to pursue different synthesis paths for b.

According to the invention, a protecting group is introduced in the resulting alcohol b in step ii.

THP, MTM, TBDMS, TBDPS, general silyl protecting groups, or MOM may be used as protecting groups.

In addition, p-toluene sulfonic acid can be added as a catalyst.

The solvent used can be dichloromethane, DMF, or tetrahydrofurane.

The reaction temperature preferably ranges between 0° C. and room temperature, for example 17° C. to 25° C.

In a subsequent step iii, the substituent $R^1$ of compound c is replaced by a formyl group.

The formylation can be carried out, for example, using anilide, formyl piperidine or dimethylformamide in the presence of metallizing reagents, such as sec-butyl lithium, n-butyl lithium, tert-butyl lithium, lithium or magnesium.

The solvent used can be tetrahydrofurane or another ether, for example.

The reaction can be carried out in a temperature range between −20° C. and −80° C., preferably between −50° C. and −80° C., with −78° C. being particularly preferred, this being the dry ice temperature.

The resulting compound d is reduced to an alcohol e in a subsequent step iv.

The reducing agent used can be a metal hydride, such as sodium borohydride or lithium aluminum hydride, for example.

Suitable solvents are methanol or other alcohols, such as ethanol, propanol or isopropanol, in particular when using sodium borohydride.

The reaction is preferably carried out at room temperature.

The alcohol e is halogenated or tosylated into compound f in the subsequent reaction v, wherein the tosyl group takes the place of Br in formula f.

For this purpose, preferably tetrabromomethane is used in the presence of triphenylphosphine as an oxygen scavenger.

The solvent used can be dichloromethane or in general halogenated hydrocarbons.

The preferred temperature is between 0° C. and approximately 4° C.

In reaction step vi, compound f is converted using a chiral amino acid reagent. To this end, compound f is converted using (S)-BOC-BMI: (S)-1-(tert-butoxycarbonyl)-2-tert-butyl-3-methyl-4-imidazolidinone, (S)-Cbz-BMI: (S)-1-(benzoylcarbonyl)-2-tert-butyl-3-methyl-4-imidazolidinone, (S)-BDI: (S)-tert-butyl 2-tert-butyl-4-methoxy-2,5-dihydroimidazol-1-carboxylate, methyl-(S)-BOC-BMI: (2S, 5R)-tert-butyl-2-tert-butyl-3,5-dimethyl-4-oxoimidazolidine-1-carboxylate, methyl-(S)-Cbz-BMI: (S)-1-(benzoylcarbonyl)-2-tert-butyl-3,5-dimethyl-4-imidazolidinone, or methyl-(S)-BDI: (S)-tert-butyl-2-tert-butyl-5-methyl-4-methoxy-2-hydroimidazol-1-carboxylate.

The conversion can be carried out in the presence of lithium diisopropylamine.

The solvent used can be tetrahydrofurane or an ether, preferably diethylether, or at least one constituent of this class.

The resulting compound g is deprotected on the $OR^2$ function in step vii. For this purpose, pyridinium-p-toluene sulfonic acid can be used, for example. However, it is possible to employ any known method for removing the protecting group, such as the use of acids or $MgBr_2$.

Possible solvents are alcohols, such as ethanol, methanol, propanol or isopropanol.

The reaction product h is oxidized into an aldehyde in step viii.

For this purpose, known mild oxidation methods may be employed.

For this purpose, by way of example, Swern oxidation can be performed. The conversion is carried out using oxalyl chloride or dimethyl sulfoxide in the presence of triethylamine.

The reaction is carried out in a range of −20° C. to −80° C., −30° C. to −80° C., or preferably between −50° C. and −80° C. Typically it is conducted at the dry ice temperature of approximately −78° C.

The solvent used can be halogenated hydrocarbon, such as dichloromethane.

The reaction product is the precursor of formula 3 according to the invention.

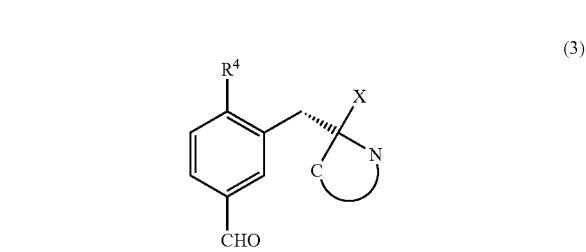

(3)

In a further conversion, the precursor having formula 3 can be converted into 2-[$^{18}$F]FPhe or 6-[$^{18}$F]FMT.

For this purpose, the position of the substituent $R^4$ of the precursor according to formula 3 is $^{18}$F-fluoridated. This fluoridation can be attained using standard methods. To this end, the phase transfer catalysts Kryptofix potassium oxalate, Kryptofix potassium carbonate, or tetrabutyl ammonium hydrogen carbonate can be employed as the anion activator for $^{18}$F$^-$.

The $^{18}$F-fluoridated intermediate product is separated in a further step. In the case of the 6-[$^{18}$F]FMT, the $^{18}$F-fluoridated intermediate product is oxidized into ester.

The separation can be carried by way of solid phase extraction. For this purpose, the reaction mixture is purified using a reverse-phase cartridge.

The oxidation of the aldehyde group can be carried out, for example, using mCPBA or peracetic acid or perborate, but other oxidizing agents are also possible. The solvents used can be halogenated hydrocarbons, such as chloroform or methylene chloride.

In the case of the 2-[$^{18}$F]FPhe, instead of oxidation, decarbonylation is carried out.

Advantageously, suitable catalysts for the decarbonylation notably comprise one or more transition metals of the secondary groups I, II, VI, VII, and VIII, such as chromium, manganese, nickel, copper or zinc, and preferably one or more metals from the group consisting of the platinum metals, in particular rhodium. In a heterogeneous system, solid catalysts on carriers may be used, or in homogeneous systems, this can be carried out in the liquid phase.

Soluble rhodium complexes, which can be used in a homogeneous liquid system or by which carriers can be impregnated, are, for example, rhodium(I) complexes such as ClRh (PPh$_3$)$_3$ ("Wilkinson catalyst"), ClRh(CO) (PPh$_3$)$_2$, [ClRh (CO)$_2$]$_2$, acacRh(CO)(PPh$_3$), acacRh(CO)$_2$, (C$_5$H$_5$)Rh (C$_8$H$_{14}$) and (C$_3$H$_5$)Rh(PPh$_3$), where Ph is phenyl, acac is acetylacetonate, C$_8$H$_{14}$ cyclooctene, C$_5$H$_5$ cyclopentadienyl, and C$_3$H$_5$ is allyl. Also suited are rhodium(II) and rhodium (III) complexes, such as rhodium(II)-acetate, rhodium(II)-2, 4-difluorobenzoate, Rh(acac)$_3$, RhCl$_3$·xH$_2$O, Rh(NO$_3$)$_3$ and (C$_3$H$_5$)RhCl$_2$(PPh$_3$)$_2$. Advantageously, compounds which can act as ligands, such as phosphanes, phosphites or amines, may be added to these rhodium complexes.

In a further step, the product that is obtained from the oxidation or decarbonylation is subjected to hydrolysis, whereby 2-[$^{18}$F]FPhe or 6-[$^{18}$F]FMT or the α-methylated derivative thereof is obtained.

Hydrolysis can be carried out in an aqueous solution, preferably concentrated HI or HBr or in a solution with KI or HBr.

The product can be separated using HPLC.

Another object of the invention is the compound according to formula 3, where

X=H or CH$_3$ and

R$^4$=nucleophilic leaving group, such as F, Br, Cl, NO$_2$, —NR$_3^+$, where R=alkyl, such as CH$_3$, C$_2$H$_5$, and R$^3$=(S)-BOC-BMI: (S)-1-(tert-butoxycarbonyl)-2-tert-butyl-3-methyl-4-imidazolidinone, (S)-Cbz-BMI: (S)-1-(benzoylcarbonyl)-2-tert-butyl-3-methyl-4-imidazolidinone, (S)-BDI: (S)-tert-butyl 2-tert-butyl-4-methoxy-2,5-dihydroimidazol-1-carboxylate, methyl-(S)-BOC-BMI: (2S, 5R)-tert-butyl-2-tert-butyl-3,5-dimethyl-4-oxoimidazolidine-1-carboxylate, methyl-(S)-Cbz-BMI: (S)-1-(benzoylcarbonyl)-2-tert-butyl-3,5-dimethyl-4-imidazolidinone, or methyl-(S)-BDI: (S)-tert-butyl-2-tert-butyl-5-methyl-4-methoxy-2-hydroimidazol-1-carboxylate.

Formula notation:

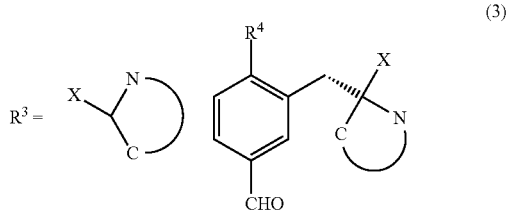

(3)

(precursor)

By using the novel labeling precursor, it is possible to produce enantiopure products having formulas 1 and 2 (ee≧98%) by way of a nucleophilic synthesis using only three radioactive steps. This allows for automated routine synthesis of the compounds according to formulas 1 and 2. The precursor is also obtained at an enantiomeric purity of ≧98%.

The method according to the invention and the precursor according to formula 3 allow synthesis to be carried out remotely or completely automatically starting with the nuclide production of $^{18}$F$^-$.

In general, apparatuses for an automated synthesis comprise a charge vessel, which is supplied with reagents from reservoir vessels using a control unit, the reservoir vessels being connected to the charge vessel by way of feed lines. The charge vessel is generally filled and emptied by generating a positive pressure or a negative pressure. By way of example, the commercially available apparatus TRACERlab FX F-N shall be mentioned, in which in addition to reservoir vessels for reagents, a charge vessel made of glass carbon fibers, magnetic stirrer, and a pull-out needle is equipped with an activity detector and a vacuum system having a cooling trap. The apparatus comprises an $^{18}$O water processing unit and a solid phase extraction unit with preparative HPLC, two HPLC eluents and HPLC flow control, UV and radio activity detectors for the HPLC, collection vessels for fractions, solid phase extraction and HPLC solvent recirculation. Similar apparatuses are known from "One-step high-radiochemical-yield synthesis of [$^{18}$F]FP-CIT using a protic solvent System" in Nuc. Med. Biol., 2007; 34: 345-351 by S. Lee, S Oh, D. Chi, S. Kang, H. Kil, J Kim, D. Moon and furthermore from Chen X, Park R, Shahinian A H, et al. $^{18}$F-labeled RGD peptide: initial evaluation for imaging brain tumor angiogenesis /Nuc. Med. Biol., 2004; 31: 179-189.

The precursor according to the invention allows fully automated implementation of such a system, in which an $^{18}$F fluoridation of the precursor according to formula 3 is carried out and thereafter the processing into the end product, which is 2-[$^{18}$F]FPhe or 6-[$^{18}$F]FMT, takes place. 2-[$^{18}$F]FPhe and 6-[$^{18}$F]FMT are obtained in an enantiomeric purity of ≧98%.

EXAMPLE 1

The synthesis according to FIG. 1 can be carried out using the following reagents:

i) Methanol, sodium borohydride ii) Dichloromethane, dihydropyrane, p-toluene sulfonic acid iii) Tetrahydropyrane, sec-butyl lithium, dimethylformamide iv) Methanol, sodium borohydride v) Dichloromethane, tetrabromomethane, triphenylphosphine vi) Tetrahydropyrane, lithium diisopropylamine, (S)-Boc-BMI vii) Ethanol, pyridinium-p-toluene sulfonic acid viii) Dichloromethane, oxalyl chloride, dimethyl sulfoxide, triethylamine Specific Exemplary Embodiment (3-bromo-4-fluoro-phenyl)-methanol A solution of 5 g (24.6 mmol) 3-bromo-4-fluoro-benzaldehyde in 20 ml anhydrous methanol is mixed in portions with 1.38 g (36.58 mmol) sodium borohydride while stirring and stirred for another hour at room temperature. After adding water, an extraction is carried out using diethyl ether, and the organic phase is dried over sodium sulfate. After the solvent is removed under vacuum, the appropriate alcohol is obtained. The product is obtained in pure form and can be used for further reactions.

Form: colorless crystals

Yield: 4.68 g (22.9 mmol; 93%)

$R_f$: 0.41 (diethyl ether/n-hexane=1:1)

2-(3-bromo-4-fluoro-benzyloxy)-tetrahydropyrane

A solution of 5 g (24.39 mmol) (3-bromo-4-fluoro-phenyl)-methanol and 5.6 ml (60.98 mmol) 3,4-dihydro-2H-pyrane in 50 ml absolute dichloromethane is mixed at 0° C. with a small amount covering the tip of a spatula of toluene sulfonic acid monohydrate and stirred for 15 minutes. After 2 hours of stirring at room temperature, it is mixed with diethyl ether. The organic phase is separated off, washed with a sodium chloride and sodium carbonate solution and water, and then again with a sodium chloride solution, dried over sodium sulfate, and the solvent is removed under vacuum. The resulting raw product is purified by way of column chromatography on silica gel using diethyl ether/n-hexane (1:3).

Form: colorless oil

Yield: 6.42 g (22.19 mmol; 91%)

$R_f$: 0.78 (diethyl ether/n-hexane=1:1)

2-fluoro-5-(tetrahydropyrane-2-yloxymethyl)-benzaldehyde 6.42 g (22.19 mmol) 2-(3-bromo-4-fluorobenzyloxy)tetrahydropyrane is dissolved in 50 ml absolute THF, slowly mixed with 19.2 ml sec-BuLi (1.4 M in cyclohexane) at −78° C. under an argon atmosphere, and stirred for 45 minutes. After adding 2.6 ml (33.83 mmol) DMF, the reaction solution is stirred for another 60 minutes at room temperature. After adding water, extraction is performed using diethyl ether, and the organic phase is dried over sodium sulfate. After removing the solvent under vacuum, the raw product is purified by way of column chromatography on silica gel using diethyl ether/n-hexane (1:1).

Form: yellow oil

Yield: 2.5 g (10.49 mmol; 47%)

$R_f$: 0.68 (diethyl ether/n-hexane=1:1)

[2-fluoro-5-(tetrahydropyrane-2-yloxymethyl)-phenyl]-methanol

A solution of 2.5g (10.49 mmol) 2-fluoro-5-(tetrahydropyrane-2-yloxymethyl)-benzaldehyde in anhydrous methanol is mixed in portions with 0.60 g (15.7 mmol) sodium borohydride while stirring and stirred for another hour at room temperature. After adding water, extraction is performed using diethyl ether, and the organic phase is dried over sodium sulfate. After removing the solvent under vacuum, the benzyl alcohol is obtained in pure form.

Form: colorless oil

Yield: 2.04 g (8.49 mmol; 81%)

$R_f$: 0.25 (diethyl ether/n-hexane=1:1)

2-(3-bromomethyl-4-fluorobenzyloxy)-tetrahydropyrane 4.44 g (16.94 mmol) triphenylphosphine in 10 ml dichloromethane is added in drops to an ice-cold solution of 3 g (12.49 mmol) [2-fluoro-5-(tetrahydropyrane-2-yloxymethyl)-phenyl]methanol and (15.61 mmol) tetrabromomethane in 30 ml anhydrous dichloromethane and stirred for another 45 minutes at 0° C. The reaction solution is mixed with pentane, the precipitation is suctioned off and washed with dichloromethane. The filtrate is washed with 5% sodium hydrogen carbonate solution, water and sodium chloride solution and dried over magnesium sulfate. After removing the solvent, the residue is purified by way of column chromatography on silica gel using diethyl ether/petrol ether 1:10.

Form: colorless oil

Yield: 1.85 g (6.1 mmol; 49%)

$R_f$: 0.21 (diethyl ether/petroleum ether=1:10)

(2S,5S)-2-tert-butyl-5-[2-fluoro-5-(tetrahydro-2H-pyrane-2-yloxymethyl)-benzyl]-3-methyl-4-oxoimidazoline-1-carboxylic acid-tert-butyl ester 2.6 ml (3.9 mmol) LDA is added to a solution of 1 g (3.9 mmol) (S)-BOC-BMI in 20 ml anhydrous THF at −78° C. under argon atmosphere and stirred for 40 minutes. After adding 1.18 g (3.9 mmol) 2-(3-bromomethyl-4-fluoro-benzyloxy)-tetrahydropyrane, the reaction solution is stirred for 18 hours at room temperature, mixed with saturated ammonium chloride solution, and taken up in diethyl ether and water. The aqueous phase is extracted twice using diethyl ether; the combined purified organic extracts are dried over sodium sulfate, and the solvent is reduced under vacuum. The raw product is purified by way of column chromatography on silica gel using diethyl ether/petroleum ether 2:1.

Form: colorless oil

Yield: 0.43 g (0.89 mmol; 23%)

$R_f$: 0.58 (diethyl ether/petroleum ether=2:1)

(2S,5S)-2-tert-butyl-5-(2-fluoro-5-hydroxymethyl-benzyl)-3-methyl-4-oxoimidazoline-1-carboxylic acid-tert-butyl ester 0.43 g (0.89 mmol) (2S,5S)-2-tert-butyl-5-[2-fluoro-5-(tetrahydro-2H-pyrane-2-yloxymethyl)-benzyl]-3-methyl-4-oxoimidazoline-1-carboxylic acid-tert-butyl ester is dissolved in 10 ml ethanol and stirred with 23 mg (0.09 mmol) pyridinium-p-toluene sulfonate overnight at 60° C. After cooling, the reaction mixture is taken up in diethyl ether, washed with sodium chloride solution and dried over sodium sulfate. Thereafter, the volatile constituents are removed under vacuum.

Yield: 0.34 g (0.88 mmol; 99%)

Form: colorless oil $R_f$: 0.29 (diethyl ether/n-hexane=10:1)

(2S,5S)-2-tert-butyl-5-(2-fluoro-5-formyl-benzyl)-3-methyl-4-oxoimidazolin-1-carboxylic acid-tert-butyl ester Under an argon atmosphere, 22 µl (0.26 mmol) oxalyl chloride in 2 ml dichloromethane is slowly mixed with 41 µl (0.58 mmol) dimethyl sulfoxide at −60° C. and stirred for 10 minutes. After adding 94 mg (0.24 mmol) 2-tert-butyl-5-(2-fluoro-5-hydroxymethyl-benzyl)-3-methyl-4-oxoimidazolidine-1-carboxylic acid-tert-butyl ester in 5 ml dichloromethane, this is stirred for another 15 minutes, the reaction solution is mixed with 167 µl (1.2 mmol) triethylamine, slowly heated to room temperature, and after adding 5 ml water it is stirred for another 10 minutes. The aqueous phase is separated off and extracted with dichloromethane. The organic phase is dried over sodium sulfate and the solvent is removed under vacuum. The raw product is chromatographed on silica gel using diethyl ether/n-hexane 5:1.

Form: colorless solid matter

Yield: 92 mg (0.23 mmol; 98%)

$R_f$: 0.51 (diethyl ether/n-hexane=5:1)

The invention claimed is:

1. A compound of the formula (3)

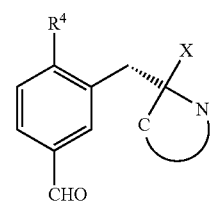

(3)

where X=H or $CH_3$ and $R^4$=nucleophilic leaving group, such as F, Br, Cl, $NO_2$, $-NR_3^+$, where R=alkyl, such as $CH_3$, $C_2H_5$, and $R^3 =$ 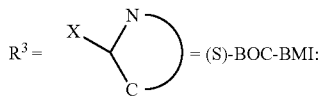 $= (S)\text{-BOC-BMI}$:

(S)-1-(tert-butoxycarbonyl)-2-tert-butyl-3-methyl-4-imidazolidinone, (S)-Cbz-BMI: (S)-1-(benzoylcarbonyl)-2-tert-butyl-3-methyl-4-imidazolidinone, (S)-BDI: (S)-tert-butyl 2-tert-butyl-4-methoxy-2,5-dihydroimidazol-1-carboxylate, methyl-(S)-BOC-BMI: (2S,5R)-tert-butyl-2-tert-butyl-3,5-dimethyl-4-oxoimidazolidine-1-carboxylate, methyl-(S)-Cbz-BMI: (S)-1-(benzoylcarbonyl)-2-tert-butyl-3,5-dimethyl-4-imidazolidinone, or methyl-(S)-BDI: (S)-tert-butyl-2-tert-butyl-5-methyl-4-methoxy-2-hydroimidazol-1-carboxylate.

2. A method for producing the compound according to formula (3)

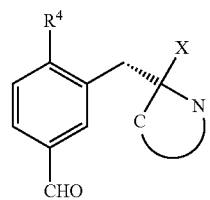

(3)

where X=H or $CH_3$ and
$R^4$=nucleophilic leaving group, such as F, Br, Cl, $NO_2$, $-NR_3^+$, where R=alkyl, such as $CH_3$, $C_2H_5$, and $R^3 =$ 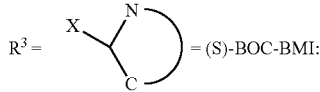 $= (S)\text{-BOC-BMI}$:

(S)-1-(tert-butoxycarbonyl)-2-tert-butyl-3-methyl-4-imidazolidinone, (S)-Cbz-BMI: (S)-1-(benzoylcarbonyl)-2-tert-butyl-3-methyl-4-imidazolidinone, (S)-BDI: (S)-tert-butyl 2-tert-butyl-4-methoxy-2,5-dihydroimidazol-1-carboxylate, methyl-(S)-BOC-BMI: (2S,5R)-tert-butyl-2-tert-butyl-3,5-dimethyl-4-oxoimidazolidine-1-carboxylate, methyl-(S)-Cbz-BMI: (S)-1-(benzoylcarbonyl)-2-tert-butyl-3,5-dimethyl-4-imidazolidinone, or methyl-(S)-BDI: (S)-tert-butyl-2-tert-butyl-5-methyl-4-methoxy-2-hydroimidazol-1-carboxylate, wherein in a step (ii) a compound (b)

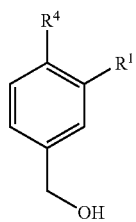

(b)

where $R^4$=nucleophilic leaving group, such as F, Br, Cl, $NO_2$, $-NR_3^+$, where R=alkyl, such as $CH_3$, $C_2H_5$ $R^1$=Br or I is converted into compound (c) by introducing a protecting group

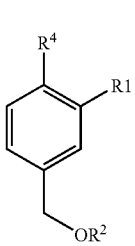

(c)

where $R^2$=tetrahydropyranyl (THP), methylthiomethyl (MTM), methoxymethyl (MOM), TBDMS, TBDPS, or a general silyl protecting group, whereupon in a further step (iii) in compound (c) the substituent $R^1$ is replaced by a formyl group forming compound (d)

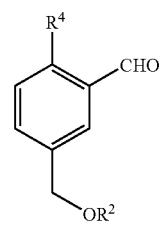

(d)

in a step (iv) the formyl group in compound (d) is reduced to an alcohol, whereby the product (e)

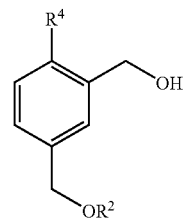

(e)

is produced
in a further step (v) the compound according to formula (e) is halogenated into compound (f), wherein, as an alternative, instead of the Br group, a tosyl group can be introduced by tosylation,

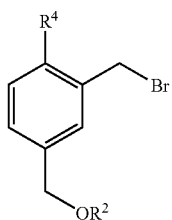

(f)

which in a further reaction (vi) is converted into product (g)

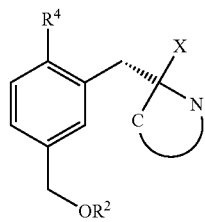

(g)

using a chiral reagent selected from the group consisting of (S)-BOC-BMI: (S)-1-(tert-butoxycarbonyl)-2-tert-butyl-3-methyl-4-imidazolidinone, (S)-Cbz-BMI: (S)-1-(benzoylcarbonyl)-2-tert-butyl-3-methyl-4-imidazolidinone, (S)-BDI: (S)-tert-butyl 2-tert-butyl-4-methoxy-2,5-dihydroimidazol-1-carboxylate, methyl-(S)-BOC-BMI: (2S,5R)-tert-butyl-2-tert-butyl-3,5-dimethyl-4-oxoimidazolidine-1-carboxylate, methyl-(S)-Cbz-BMI: (S)-1-(benzoylcarbonyl)-2-tert-butyl-3,5-dimethyl-4-imidazolidinone, or methyl-(S)-BDI: (S)-tert-butyl-2-tert-butyl-5-methyl-4-methoxy-2-hydroimidazol-1-carboxylate, in a further step (vii) by removing the protecting group $R^2$ the compound (g) is converted into compound (h)

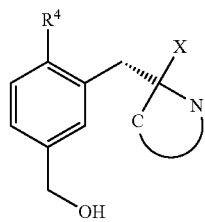

(h)

which in step (viii) is converted by oxidation at the alcohol function into the aldehyde according to formula (3)

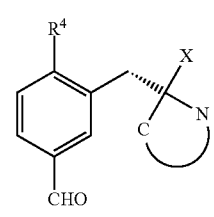

.

3. A method for producing a compound according to formula (1) or (2),

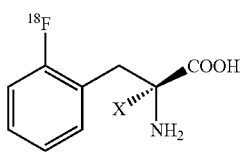

(1)

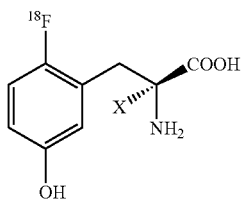

(2)

where X=H or $CH_3$ wherein the compound according to formula (3) according to claim 1 is $^{18}F$-fluoridated, separated off in a further step, and is oxidized if the compound according to formula (2) is produced, and is decarbonylated if the compound according to formula (1) is produced, and the resulting product is hydrolyzed and isolated.

4. The method according to claim 3, wherein the $^{18}F$-fluoridated is carried out using a phase transfer catalyst as an anion activator.

5. The method according to claim 3 or 4, wherein the separation of the $^{18}F$-fluoridated product is carried out by way of solid phase extraction.

6. A method according to claim 3 or 4, wherein the formyl group is oxidized into an ester if the compound according to formula (2) is produced.

7. The method according to claim 6, wherein the oxidation is carried out using mCPBA or peracetic acid or perborate.

8. A method according to claim 3 or 4, wherein the $^{18}F$-fluoridated precursor is decarbonylated by way of a catalyst to produce the compound according to formula (1).

9. A method according to claim 3 or 4, wherein the product is separated by way of HPLC.

10. A method according to claim 5, wherein the formyl group is oxidized into an ester if the compound according to formula (2) is produced.

11. The method according to claim 5, wherein the oxidation is carried out using mCPBA or peracetic acid or perborate.

12. A method according to claim 5, wherein the $^{18}F$-fluoridated precursor is decarbonylated by way of a catalyst to produce the compound according to formula (1).

13. A method according to claim 5, wherein the product is separated by way of HPLC.

14. A method according to claim 6, wherein the product is separated by way of HPLC.

15. A method according to claim 7, wherein the product is separated by way of HPLC.

16. A method according to claim 8, wherein the product is separated by way of HPLC.

* * * * *